United States Patent [19]

Yen

[11] 4,203,990
[45] May 20, 1980

[54] ANTI-DIARRHEAL 2-SUBSTITUTED QUINUCLIDINES

[75] Inventor: Chung H. Yen, Arlington Heights, Ill.

[73] Assignee: G. D. Searle & Co., Skokie, Ill.

[21] Appl. No.: 34,890

[22] Filed: Apr. 30, 1979

[51] Int. Cl.$^2$ .................. A61K 31/445; C07D 453/02
[52] U.S. Cl. ...................................... 424/267; 546/133
[58] Field of Search ................................ 546/112, 133

[56] References Cited

U.S. PATENT DOCUMENTS

| | | | |
|---|---|---|---|
| 3,917,615 | 11/1975 | Adelstein | 424/267 X |
| 3,998,832 | 12/1976 | Adelstein et al. | 424/267 X |
| 4,013,667 | 3/1977 | Yen | 546/133 |
| 4,017,491 | 4/1977 | Adelstein | 424/267 X |
| 4,086,234 | 4/1978 | Dryden et al. | 260/326.5 D X |
| 4,125,531 | 11/1978 | Yen | 546/133 |

OTHER PUBLICATIONS

Adelstein, G., et al., J. Med. Chem., 19(10), 1221–1225 (1976).
Martensson, Acta Chem. Scand. 19(3), 711 (1965).

*Primary Examiner*—Henry R. Jiles
*Assistant Examiner*—Richard A. Schwartz
*Attorney, Agent, or Firm*—Michael T. Murphy; Albert Tockman

[57] ABSTRACT

The present invention provides 2-substituted quinuclidines of the formula

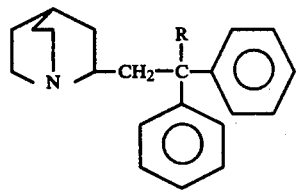

and the pharmaceutically acceptable acid addition salts thereof wherein R is phenyl, halogen-substituted phenyl, lower alkyl-substituted phenyl, pyridyl or 5-methyl-1,3,4-oxadiazol-2-yl.

These quinuclidine compounds are useful as anti-diarrheal agents.

9 Claims, No Drawings

ANTI-DIARRHEAL 2-SUBSTITUTED QUINUCLIDINES

DETAILED DESCRIPTION OF THE INVENTION

The present invention encompasses 2-Substituted quinuclidines characterized by the formula (I)

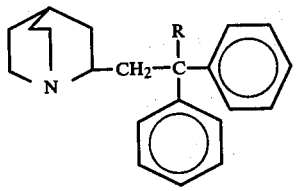

(I)

and the pharmaceutically acceptable acid addition salts thereof wherein R is phenyl, halogen-substituted phenyl, lower alkyl-substituted phenyl, pyridyl or 5-methyl-1,3,4-oxadiazol-2-yl.

The term "halogen", as used herein, includes chlorine, fluorine, bromine and iodine.

As used herein, the term "lower alkyl" refers to both straight and branched chain alkyl radicals having from 1 to 4 carbon atoms which include methyl, ethyl, propyl, isopropyl, butyl, and the like.

The present compounds exhibit anti-diarrheal activity and are quite useful in the treatment of mammals having diarrhea.

According to the present invention, in the treatment of diarrhea, an effective anti-diarrheal amount to be administered to a mammal ranges from about 0.1 to about 25.0 mg./kg. of a quinuclidine compound.

The compounds of the present invention may be prepared by the method set forth below in Scheme I:

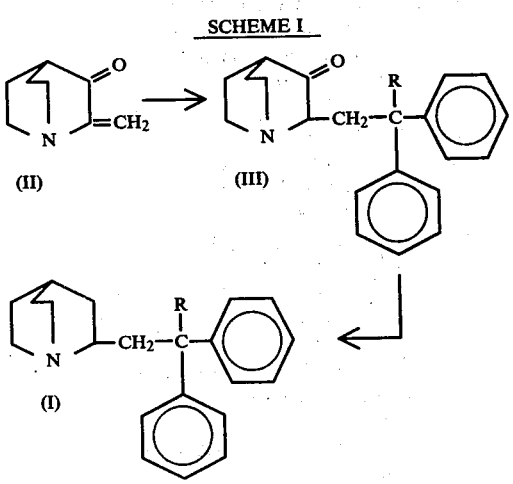

wherein R is a phenyl, substituted phenyl or pyridyl group.

SCHEME I

In this method, 2-methylene-3-quinuclidinone (II) is treated with a lithium salt of triphenylmethane or diphenyl-pyridylmethane generated in situ to provide an intermediate compound (III). The intermediate compound (III) is then treated with a solution of $H_2NNH_2 \cdot H_2O$ and KOH in diethylene glycol to provide the product, compound (I), e.g., 2-(2,2,2-triphenylethyl)-1-azabicyclo[2.2.2]octane.

A detailed description of this method is set forth below in the Examples.

In an alternate method, compounds wherein R is 5-methyl-1,3,4-oxadiazol-2-yl, may be produced by following the reactions set forth below in Scheme II:

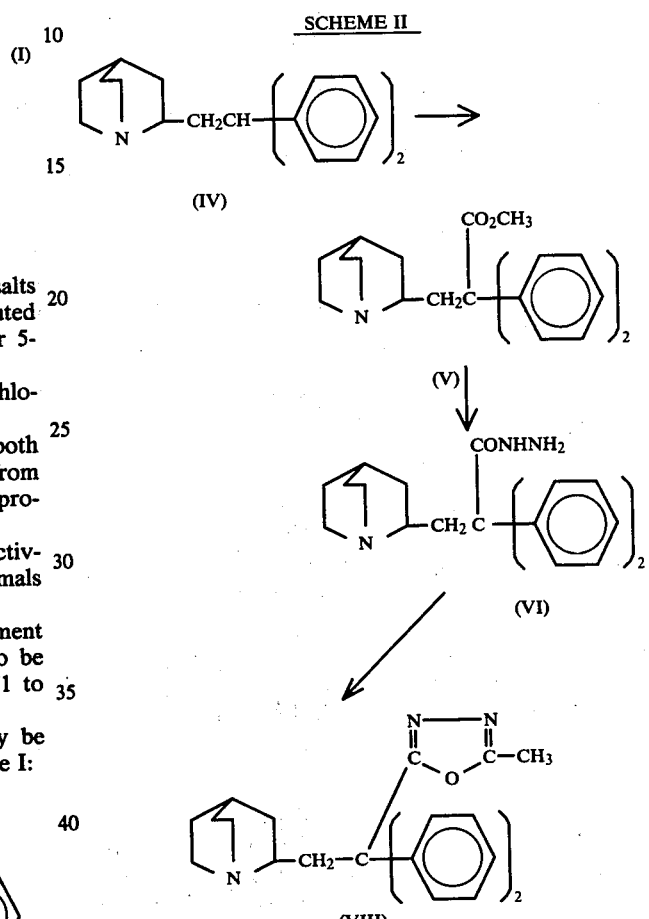

SCHEME II

According to this method, 2-(2,2-diphenylethyl)-1-azabicyclo[2.2.2]octan (IV) is treated with a butyl lithium solution in the presence of N,N,N',N-tetramethylethylenediamine followed by methyl chloroformate to yield 2,2-diphenyl-3-(1-azabicyclo[2.2.2]-oct-2-yl)propionate (V). Then the propionate (V) is treated with a solution of $H_2NNH_2$ in $CH_3OH$ to yield 2,2-diphenyl-3-(1-azabicyclo[2.2.2]-oct-2-yl)propionic acid hydrazide (VI). The hydrazide (VI) is then mixed with $CH_3C(OC_2H_5)_3$ to provide the product (VII), i.e., 2-[2-(5-methyl-1,3,4-oxadiazol-2-yl)-2,2-diphenylethyl]-1-azabicyclo 2.2.2 octane.

A detailed description of these methods is set forth below in the examples.

The compounds produced by the process schemes, illustrated above, and which are preferred embodiments within the scope of formula (I), include:

(VIII)  2-(2,2,2-triphenylethyl)-1-azabicyclo[2.2.2] octane hydrochloride

-continued

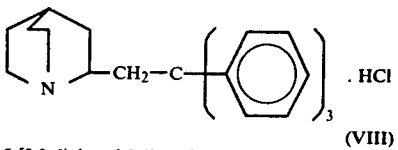

(VIII) 2-[2,2-diphenyl-2-(2-pyridyl)ethyl]-1-azabicyclo[2.2.2]octane hydrochloride

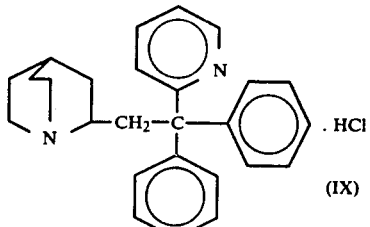

(IX) 2-[2-(5-methyl-1,3,4-oxadiazol-2-yl)-2,2-diphenylethyl]-1-azabicyclo[2.2.2]octane hydrochloride.

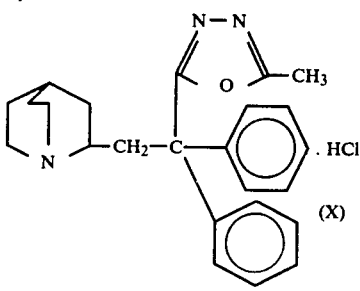

The present compounds are potent anti-diarrheal agents as evidenced by their ability to inhibit gastrointestinal propulsive motility as set forth in the following tests:

Mouse Cecal Test

The method used for this assay is a modification of the techniques previously described by Macht and Barba-Gose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

| Compound | $ED_{50} \pm$ S.E. mg./kg. IG |
|---|---|
| 2-[(2,2,2-triphenyl)ethyl]-1-azabicyclo [2.2.2]octane hydrochloride | 0.9 ± 0.2 |
| 2-[2,2-diphenyl-2-(2-pyridyl)ethyl]-1-azabicyclo[2.2.2]octane hydrochloride | 18.1 ± 10.3 |
| 2-[2-(5-methyl-1,3,4-oxadiazol-2-yl)-2,2-diphenylethyl]-1-azabicyclo[2.2.2]octane hydrochloride | 4.4 ± 1.3 |

Castor Oil-Induced Diarrhea in the Rat

Adult Charles River male rats are fasted in community cages for 24 hours prior to the test, with free access to water. The test compound is then administered intragastrically (suspended on 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

The median effective dose at 2 hours past the castor oil administration for the following representative compound of the present invention in the castor oil-induced diarrhea in the Rat test is:

| Compound | $ED_{50} \pm$ S.E. mg./kg. IG |
|---|---|
| 2-(2,2,2-triphenylethyl)-1-azabicyclo[2.2.2]octane hydrochloride | 0.20 ± 0.05 |

The compounds herein described can be combined with pharmaceutically acceptable carriers to provide normal pharmaceutical compositions. The concentration of active ingredient in the composition is not critical, but is preferably 1–80%. These compositions can be administered orally, suitable forms for each administration including tablets, lozenges, capsules, degrees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil, olive oil, corn oil, oil of theobroma; water; agar; alginic acid; and benzyl alcohol, as well as other non-toxic compatible substances used in pharmaceutical formulations.

The compounds of this invention can be used to produce an anti-diarrheal effect in mammals by administering the instant novel compositions containing a therapeutically effective amount of the active ingredient. The term "therapeutically effective amount" is defined as the amount of active ingredient that will produce an anti-diarrheal effect, i.e., which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard for which the therapeutic dosage is known. Typically 0.1–25 mg./kg. is an effective anti-diarrheal amount of a given compound.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade (°C.).

EXAMPLE 1

2-methylene-3-quinuclidinone (II)

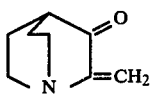

The process, described below, for preparing 2-methylene-3-quinuclidinone is a modification of the process of A. R. Hanson and H. Bader, as recorded in the *Journal of Heterocyclic Chemistry*, Vol. 3, p. 109 (1966).

52 grams (0.32 mol) of Quinuclidine-3-one HCl is dissolved in a minimum amount of water. This water solution is then treated with an excess of $K_2CO_3$ forming a slurry which is cooled. The slurry is extracted repeatedly with diethyl ether. The combined extracts are stripped in vacuo to provide a white solid. This solid, $(CH_3)_2NH.HCl$ (39 g., 0.48 mol) and 37% $H_2CO$ (39 g.) are then dissolved in 50 ml. of ethanol. KOH (30 g., 0.48 mol) in pellet form in 50 ml. $H_2O$ is added to the dissolved white solid and stirred under nitrogen and a reflux condenser. This mixture is heated at 70° with stirring for 18 hours. Then, the mixture is cooled and stripped in vacuo. The residue is treated with a large amount of $K_2CO_3$ and extracted with diethyl ether repeatedly. The combined extracts are dried with $Na_2SO_4$ and stripped in vacuo (water pump). The residue is distilled to provide 27 g. of 2-methylene-3-quinuclidinone as a greenish yellow oil (b.p. 83°–85° at 5 mm Hg) having a density of 1.072.

EXAMPLE 2

2-[(2,2,2-triphenyl)ethyl]-1-azabicyclo[2.2.2]octane-3-one hydrochloride (XI)

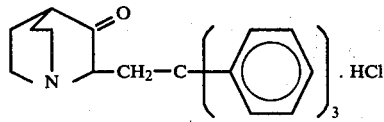

34.4 ml. of butyl lithium (1.6 M) in hexane is added dropwise to a stirred solution of 12.2 g. (0.05 mol) of triphenylmethane and 7.52 ml. (0.05 mol) of N,N,N',N'-tetramethylethylenediamine in 400 ml. of dry diethyl ether at 5°–10° under argon, using an ice-water cooling bath. The reaction mixture is stirred in the bath for ½ hour, and then stirred at ambient temperature with the cooling bath removed for 1 hour, resulting in a red mixture containing a red solid precipitate.

To the reaction mixture is added 6.5 ml. (0.05 mol) of 2-methylene-3-quinuclidinone (II) during a period of 3 minutes, the reaction being only slightly exothermic. This mixture is stirred for 18 hours, washed with water 8 times, and then extracted with dilute HCl. The dilute HCl extract is made strongly alkaline with an aqueous solution of NaOH, liberating an oil, and extracted with diethyl ether. The ethereal extract is then washed with a saturated NaCl solution, dried with $Na_2SO_4$ and stripped in vacuo providing 7.9 grams of a thick oil.

The thick oil is dissolved in 100 ml. of dry diethyl ether, and then treated with a slight excess of HCl/isopropional (7.5 N). The precipitated gum is separated and washed with diethyl ether. The gum solidifies upon stirring with 25 ml. of acetone. The solid is filtered off, washed with acetone, and air-dried to provide 4.18 grams of a white solid. The white solid is dissolved in 125 ml. of $CH_2Cl_2$. After filtration, the filtrate is concentrated to about 15 ml. and then diluted with 150 ml. of acetone and allowed to crystallize. The crystals are collected by suction and dried in vacuo to provide 2.61 grams of 2-(2,2,2-triphenylethyl)-1-azabicyclo[2.2.2]octane-3-one hydrochloride (XI) as a white solid melting at about 243°–246°.

EXAMPLE 3

2-(2,2,2-triphenylethyl)-1-azabicyclo[2.2.2] octane hydrochloride (VIII)

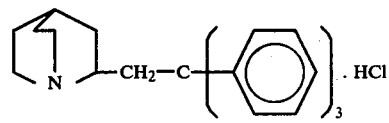

A mixture of 2.25 grams (5.38 mmol) of 2-(2,2,2-triphenylethyl)-1-azabicyclo[2.2.2]octane-3-one hydrochloride (XI), 1.14 grams (19.4 mmol) 85% $H_2NNH_2.H_2O$, 1.5 grams (23 mmol) 85% KOH and 160 ml of diethylene glycol is heated to reflux for 2 hours. The resultant solution is cooled to room temperature and poured into 1.0 liter of ice-water. The aqueous layer has a pH of about 12.0 which is adjusted to about 14.0 with aqueous KOH. The solution is extracted twice with diethyl ether, and the combined ether extracts are shaken with dilute HCl (400 ml. containing 4 ml. of concentrated HCl) resulting in the formation of a fine solid precipitate. The precipitate is filtered and washed with water and diethyl-ether, and air-dried to provide 892 mg. of a white powder. The white powder is recrystallized from methanolether and dried in vacuo (0.1 mm. Hg) at 100° for 18 hours and then at 140° for 2 hours to provide the product, 2-(2,2,2-triphenylethyl)-1-azabicyclo[2.2.2]octane hydrochloride (VIII); MW:403.99.

EXAMPLE 4

2-[2,2-diphenyl-2-(2-pyridyl)ethyl]-1-azabicyclo[2.2.2]octan-3-one (XII)

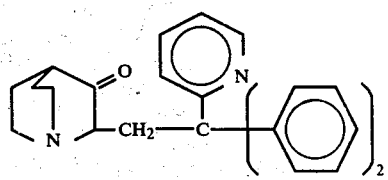

78.8 ml. (126 mmol) of a 1.6 M solution of butyl lithium in hexane is added during 5 min. to diphenyl-2- pyridylmethane in 400 ml. of dry diethyl ether with stirring under nitrogen. The reaction mixture turned red immediately after the beginning of the addition and reached reflux during the addition. The mixture is stirred at ambient temperature for 40 minutes to provide a deep red solution.

16.1 ml. (126 mmol) of 2-methylene-2-quinuclidinone (II) is added to the solution at 20°-25°, using a cold-water bath. The red color disappears during the addition. The reaction mixture is washed with water 7 times and extracted twice with 10% $CH_3COOH$. The combined 10% acetic acid extracts are made strongly alkaline with aqueous NaOH liberating an oil. The basified $CH_3COOH$ extracts are further extracted with diethyl ether. The ethereal extract is dried with $Na_2SO_4$, and stripped in vacuo providing 33.5 g. of a gum. The gum is crystallized from ether-n-pentane and dried in vacuo (0.1 mm. Hg.) to provide 23.1 g. of a white solid product, i.e., 2-[2,2-diphenyl-2-(2-pyridyl)ethyl]-1-azabicyclo[2.2.2]octan-3-one (XII); m.p. 118°-120°; MW:382.50.

EXAMPLE 5

2-[2,2-diphenyl-2-(2-pyridyl)ethyl]-1-azabicyclo[2.2.2]octane hydrochloride (IX)

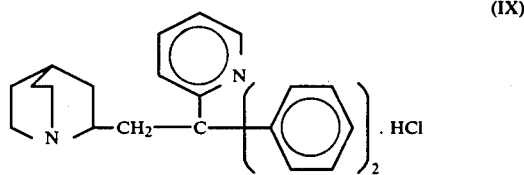

(IX)

A mixture of 7.65 grams (20 mmol) of 2-[2,2-diphenyl-2-(2-pyridyl)ethyl]-1-azabicyclo[2.2.2]octan-3-one (XII), 4.71 g. (80 mmol) of 85% $H_2NNH_2.H_2O$, 6.6 g. (100 mmol) of 85% KOH and 220 ml. diethylene glycol is heated to reflux with stirring for 2 hours under nitrogen. The mixture is cooled and poured into 1.8 liters of cold water, liberating a white material. The resulting aqueous suspension is extracted with diethyl ether. The extract is washed with water 5 times, washed with a saturated NaCl solution, dried with $Na_2SO_4$, and treated with a slight excess of HCl/isopropanol (7.0 N) causing a solid and gum precipitate. The precipitate is washed with diethyl ether and dissolved in 120 ml. of $CH_2Cl_2$. The resultant solution is diluted with 500 ml. of methylethyl/ketone and heated to distill until 25.0 ml. of volume remains. This volume is cooled to room temperature, yielding a solid and gummy precipitate which solidifies. The total solids are filtered off. The filtrate is concentrated to 15.0 ml. to yield a solid precipitate which is filtered off to provide 3.6 g. of a white solid.

The white solid is dissolved in 15 ml. of $CH_2Cl_2$ and filtered, and the filtrate diluted with 140 ml. of acetone. The solution is boiled to evaporate to 55 ml. of volume and cooled to room temperature. The crystals are filtered off, washed with acetone and dried in vacuo to yield 1.72 grams of a crude product. The mother liquor of the crude product is concentrated to yield 0.7 grams of a second batch of a crude product. The two batches of crude product are then combined and recrystallized from a mixed solvent of $CH_2Cl_2$ and acetone to provide 1.28 grams of a white solid product: 2-[2,2-diphenyl-2-(2-pyridyl)ethyl]-1-azabicyclo[2.2.2]octane hydrochloride (IX) which melts at 254°-256°.

EXAMPLE 6

Methyl 2,2-diphenyl-3-(1-azabicyclo[2.2.2]-oct-2-yl) propionate (V)

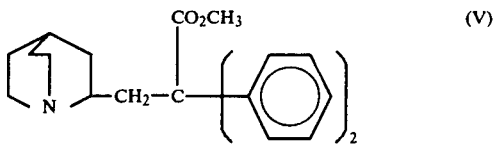

(V)

The process described below is a modification of the process disclosed in U.S. Pat. No. 4,013,667.

In this process, 16.5 g. (0.0567 mol) of 2-(2,2-diphenylethyl)-1-azabicyclo[2.2.2]octane (IV), 8.53 ml. (0.0567 mol) of N,N,N',N'-tetramethylethylenediamine, 24.0 ml. (0.0624 mol) of a 2.6 M. solution of butyl lithium in hexane and 200 ml. of cyclohexane are refluxed with stirring for 1 hr. 55 min. under argon to provide a red-orange mixture containing solid which is cooled in an ice-water bath and then in a dry ice-acetone bath. Then, when the mixture becomes very thick, 200 ml. of tetrahydrofuran is added slowly during a 40 min. period. After stirring for 10 min., 4.82 ml. (0.0624 mol) of methyl choloroformate is added during 40 min. The cooling bath is removed, and the mixture is stirred at ambient temperature for 45 min. 1.0 ml. of water is then added to the mixture which is then stripped in vacuo. The residue is partitioned between aqueous NaOH and Skelly Solve B. The Skelly Solve B layer is washed with water five times and extracted with dilute HCl. The acidic aqueous extract is made strongly alkaline with an aqueous solution of NaOH, liberating a gum which is extracted with Skelly Solve B. The Skelly Solve B extract is washed with water six times, dried with $Na_2SO_4$ and stripped in vacuo to give 18.8 g. of gum. The gum is divided into 2 equal parts. Each part is put on a 1.0 inch column of Woelm silica gel and eluted with a mixed solvent system of ethanol-toluene-conc. ammonia (volume ratio 2:98:1) under a pressure which maintains a flow rate of 10 ml./minute. The desired fractions from the 2 columns are combined and stripped in vacuo to provide 6.0 g. of oil which solidifies on standing. The solid is taken up in 600 ml. of boiling n-pentane and filtered. The filtrate is evaporated to 25 ml. and allowed to crystallize. The crystals are collected, washed with n-pentane and dried in vacuo to yield 5.61 g. of a white solid product: Methyl 2, 2-diphenyl-3-(1-azabicyclo[2.2.2]-oct-2-yl)propionate (V); m.p. 111°-112.5°; MW:349.45.

EXAMPLE 7

2,2-diphenyl-3-(1-azabicyclo[2.2.2]-oct-2-yl)propionic acid hydrazide (VI)

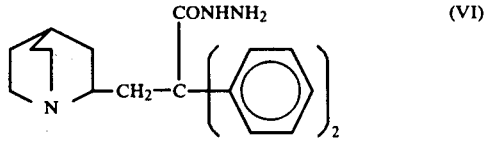

(VI)

1.0 g. of methyl 2,2-diphenyl-3-(1-azabicyclo[2.2.2]-oct-2-yl)propionate (V), 10 ml. of 85% $H_2NNH_2.H_2O$ and 16 ml. of $CH_3OH$ are heated together to reflux under nitrogen for 4 hrs. The reaction mixture is poured into 150 ml. of water and extracted with diethyl ether four times. The combined ether extracts are washed with water twice and saturated NaCl, and dried with $Na_2SO_4$. The solution is boiled down to 20 ml. and cooled to room temperature. The precipitate is filtered, washed with diethyl ether and dried in vacuo to give a product in the form of white prisms: 2,2-diphenyl-3-(1-azabicyclo [2.2.2]oct-2-yl)propionic acid hydrazide (VI); m.p. 158°-160°; MW:349.48.

EXAMPLE 8

2-[2-(5-methyl-1,3,4-oxadiazol-2-yl)-2,2-diphenylethyl]-1-azabicyclo[2.2.2]octane hydrochloride (X)

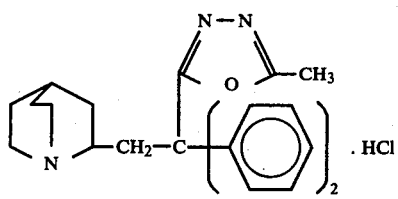
(X)

1.0 gram (2.86 mmol) of 2,2-diphenyl-3-(1-azabicyclo[2.2.2]-oct-2-yl)propionic acid hydrazide (VI) and 5.0 ml. (43 mmol) of $CH_3C(OC_2H_5)_3$ are heated to reflux under nitrogen for 18 hours. The mixture is cooled to room temperature and evaporated under vacuo (up to 0.1 mm.). Residual gum is then taken up in diethyl ether and extracted with dilute HCl. The dilute HCl extract is made strongly alkaline with an aqueous solution of NaOH and then extracted with diethyl ether. The ether extract is washed with water and with saturated NaCl, and then dried with $Na_2SO_4$. Then, the ether extract is treated with a slight excess of HCl/isopropional (7.0 N) resulting in a solid precipitate which is collected by suction, washed with diethyl ether and air-dried. The solid obtained is then recrystallized from ethanol-ether and dried in vacuo to yield 300 mg. of a white solid, m.p. 275°-277°. The white solid product is then recrystallized from ethanol-ether, dried at 100°/0.1 mm. for 2 hours to provide 260 mg. of a white solid. The white solid is then dissolved in 300 ml. of boiling acetone and filtered. The filtrate is is boiled down to about 5 ml. and allowed to crystallize. The crystals are filtered off, washed with acetone and dried in vacuo (0.1 mm) at 56° for 4 hours to provide 153 mg. of solid product, i.e., 2-[2-(5-methyl-1,3,4-oxadiazol-2-yl)-2,2-diphenylethyl]-1-azabicyclo[2.2.2]octane hydrochloride (X); m.p. 278°-280°; MW:409.96.

I claim:

1. A compound of the formula

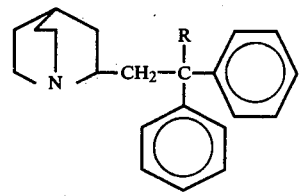

or a pharmaceutically acceptable acid addition salt thereof wherein R is phenyl, halogen-substituted phenyl, lower alkyl-substituted phenyl, pyridyl or 5-methyl-1,3,4-oxadiazol-2-yl.

2. A compound according to claim 1, which is 2-[(2,2,2-triphenyl)ethyl]-1-azabicyclo[2.2.2]octane hydrochloride.

3. A compound according to claim 1, which is 2-[2,2-diphenyl-2-(2-pyridyl)ethyl]-1-azabicyclo[2.2.2]octane hydrochloride.

4. A compound according to claim 1, which is 2-[2-(5-methyl-1,3,4-oxadiazol-2-yl)-2,2-diphenylethyl]-1-azabicyclo[2.2.2]octane hydrochloride.

5. A method of treating diarrhea comprising administering to an animal in need of anti-diarrheal treatment an effective anti-diarrheal amount of a compound of the formula

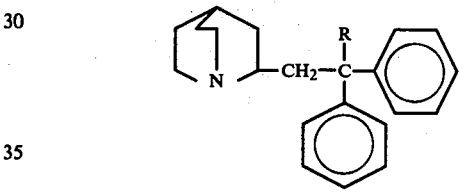

or a pharmaceutically acceptable acid addition salt thereof wherein R is phenyl, halogen-substituted phenyl, lower alkyl-substituted phenyl, pyridyl or 5-methyl-1,3,4-oxadiazol-2-yl.

6. A method according to claim 5, wherein the effective anti-diarrheal amount of said compound ranges from about 0.1 to about 25.0 mg./kg.

7. A method according to claim 5, wherein the compound is 2-(2,2,2-triphenylethyl)-1-azabicyclo[2.2.2]octane hydrochloride.

8. A method according to claim 5, wherein the compound is 2-[2,2-diphenyl-2-(2-pyridyl)ethyl]-1-azabicyclo[2.2.2] octane hydrochloride.

9. A method according to claim 5, wherein the compound is 2-[2-(5-methyl-1,3,4-oxadiazol-2-yl)-2,2-diphenylethyl]-1-azabicyclo[2.2.2]octane hydrochloride.

* * * * *